(12) United States Patent
Nakamura et al.

(10) Patent No.: US 6,759,473 B1
(45) Date of Patent: Jul. 6, 2004

(54) COATING MATERIAL AND MOLDED ARTICLE

(75) Inventors: Misao Nakamura, Kawasaki (JP); Toshihiro Inoue, Kawasaki (JP)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 10/129,956

(22) PCT Filed: Nov. 20, 2000

(86) PCT No.: PCT/JP00/08164

§ 371 (c)(1),
(2), (4) Date: May 20, 2002

(87) PCT Pub. No.: WO01/36553

PCT Pub. Date: May 25, 2001

(30) Foreign Application Priority Data

Nov. 18, 1999 (JP) .......................... 11-327825

(51) Int. Cl.$^7$ ............................................... C08L 29/04
(52) U.S. Cl. ................ 524/503; 2/161.7; 427/2.3; 428/35.2; 428/500; 428/532; 524/35; 524/43; 524/45; 524/46; 524/47; 524/52; 524/507; 524/512; 524/514; 524/515
(58) Field of Search .................... 524/503, 35, 47, 524/52, 43, 45, 46, 507, 512, 514, 515; 2/161.7; 427/2.3; 428/35.2, 500, 532

(56) References Cited

U.S. PATENT DOCUMENTS

| | | | | |
|---|---|---|---|---|
| 2,867,849 A | * | 1/1959 | Drew et al. .................. | 264/233 |
| 2,914,498 A | * | 11/1959 | Quarles et al. ............. | 524/228 |
| 3,026,531 A | * | 3/1962 | Holaday ...................... | 2/167 |
| 4,070,713 A | | 1/1978 | Stockum ...................... | 2/159 |
| 4,128,514 A | * | 12/1978 | Fitzgerald .................... | 524/43 |
| 4,923,920 A | * | 5/1990 | Scholl et al. ................ | 524/501 |
| 5,438,709 A | * | 8/1995 | Green et al. ................ | 2/167 |
| 5,444,112 A | * | 8/1995 | Carnahan ..................... | 524/272 |
| 5,649,326 A | * | 7/1997 | Richard et al. .............. | 2/161.7 |
| 5,670,263 A | * | 9/1997 | Gazeley ...................... | 428/492 |
| 5,717,031 A | * | 2/1998 | Degen et al. ............... | 525/129 |
| 5,985,955 A | * | 11/1999 | Bechara et al. ............. | 523/415 |
| 6,031,042 A | * | 2/2000 | Lipinski ...................... | 524/566 |
| 6,268,422 B1 | * | 7/2001 | Weih et al. ................. | 524/396 |

FOREIGN PATENT DOCUMENTS

| | | |
|---|---|---|
| EP | 0 407 059 A2 | 1/1991 |
| EP | 0 561 651 A1 | 9/1993 |
| JP | 7126572 A | 5/1995 |
| JP | 7145293 A | 6/1995 |
| JP | 7166075 A | 6/1995 |
| JP | 7188571 A | 7/1995 |
| JP | 8089096 A | 4/1996 |
| JP | 8294930 A | 11/1996 |
| JP | 10110399 A | 4/1998 |
| JP | 11061527 A | 3/1999 |
| JP | 7026176 A | 7/2001 |

* cited by examiner

*Primary Examiner*—Judy M. Reddick
(74) *Attorney, Agent, or Firm*—Armstrong, Kratz, Quintos, Hanson & Brooks, LLP

(57) ABSTRACT

By coating a dip-formed article with a coating agent comprising a polymer latex dispersion-stabilized with a water-soluble high-molecular-weight compound containing an alcoholic hydroxyl group, a coated article having excellent donning and putting off properties and anti-blocking property, and exhibiting greatly reduced fine particles-releasability is obtained.

15 Claims, No Drawings

COATING MATERIAL AND MOLDED ARTICLE

TECHNICAL FIELD

This invention relates to a coating agent and a coated article. More particularly, it relates to a coating agent giving a coated article by coating a dip-formed article such as a glove with the coating agent, which coated article can be easily donned and put off, from which fine particles are not easily released and which has an enhanced anti-blocking property; and to a coated article made by coating a dip-formed article with the coating agent.

BACKGROUND ART

Dip-formed articles made from natural rubber latex or synthetic rubber latex are used, for example, as rubber gloves and finger cots. In general the skin-contacting inner surface of a rubber glove is sticky and not slippery, and the rubber glove cannot be easily donned and put off. To facilitate donning and putting off of the rubber glove, various methods have been proposed. For example, to enhance the anti-sticking property, a method of applying a dusting powder such as talc powder onto the inner surface of a glove, and a method of subjecting the inner surface of a glove to a chlorinating treatment to form protrusions on the inner surface. However, in the former method, the applied dusting powder is easily released upon donning and putting off the glove, and, when the glove is used in a medical field including surgery, the released dusting powder may contaminate an operated part and cause postoperative complications. In the latter method, the treating cost is high, the facilitation of donning and putting off cannot be enhanced to the desired extent, and the use of chlorine may cause environmental pollution.

Further, proposals of enhancing donning and putting-off properties of a glove have been made wherein an elastomer layer or a resin layer, which contains fine particles incorporated therein, is formed on the inner surface of a glove. For example, a medical rubber glove has been proposed in Japanese Examined Patent Publication No. S60-6655 (U.S. Pat. No. 4,070,713), which has an inner lubricating layer formed from a latex of carboxylated styrene-butadiene rubber having starch dispersed therein. A rubber glove has been proposed in Japanese Unexamined Patent Publication (hereinafter abbreviated to "JP-A") No. H11-61527, which has an inner lubricating resin layer formed from an aqueous dispersion comprising a synthetic rubber latex and an organic filler, which rubber latex is incapable of being coagulated with a coagulant contained in a main rubber layer of the rubber glove. These proposals provide an improvement in the donning and putting-off properties to some extent, but, the surfaces of fine particles as lubricant are partly covered with a rubber latex. Thus, the improvement in donning and putting-off properties achieved is still not to the desired extent, and the inner lubricating layer tends to stick to each other and the sticking parts are difficult to separate.

A rubber glove has been proposed in JP-A H8-294930 which is made by forming on a glove form a covering resin layer from a rubber latex formulation comprising, as the principal ingredients, fine thermoplastic resin particles, a rubber latex, and a blocked isocyanate. By the use of a blocked isocyanate, adhesion of the thermoplastic resin particles to an elastomer layer formed from the rubber latex is enhanced, but, the improvement in the donning and putting-off properties is still not to the desired extent. Further, adhesion of the covering resin layer to a main rubber layer is poor, and thus, the covering resin layer tends to be separated from the main rubber layer, and pliability of the glove is liable to deteriorate due to the elastomer crosslinked with the blocked isocyanate.

DISCLOSURE OF THE INVENTION

In view of the foregoing prior art, a primary object of the present invention is to provide a dip-formed article such as, for example, a rubber glove, which can easily be donned and put off, and wherein fine particles and an elastomer ingredient not released, or are released only to a very slight extent, when the glove is donned or put off, or during wearing, and the inner elastomer coating layer exhibits an enhanced anti-blocking property; and to provide a coating agent used for the dip-formed article.

The present inventors made extensive research to achieve the above-mentioned object, and found that the aimed coated article is obtained by coating a dip-formed article with a coating agent comprising a polymer latex having incorporated there in a special dispersion stabilizer. Based on this finding, the present invention has been completed.

In accordance with the present invention, there is provided a coating agent comprising a polymer latex dispersion-stabilized with a water-soluble high-molecular weight compound having an alcoholic hydroxyl group. Preferably the coating agent further comprises fine particles.

In accordance with the present invention, there is further provided a coated article made by coating a dip-formed article with the above-mentioned coating agent.

BEST MODE FOR CARRYING OUT THE INVENTION

The polymer latex which can be used in the coating agent of the present invention is a polymer latex dispersion-stabilized with a water-soluble high-molecular weight compound having an alcoholic hydroxyl group (which compound is hereinafter referred to as "hydroxyl group-containing water-soluble polymer" when appropriate).

As specific examples of the hydroxyl group-containing water-soluble polymer, there can be mentioned vinyl alcohol polymers such as polyvinyl alcohol and various modified products thereof; alkali-soluble polymers having an alcoholic hydroxyl group; cellulose derivatives such as alkyl celluloses, hydroxyalkyl celluloses, alkylhydroxyalkyl celluloses and carboxymethyl cellulose; starch derivatives such as alkyl starches, carboxymethyl starch and oxidized starch; arabian gum and tragacanth gum; and polyalkylene glycols. Of these, vinyl alcohol polymers and alkali-soluble polymers having an alcoholic hydroxyl group are preferable because industrially quality-stabilized products thereof are easily available. Vinyl alcohol polymers are especially preferable because their coating layers have excellent water-resistance.

The hydroxyl group-containing water-soluble polymer preferably has a molecular weight (weight average molecular weight) of at least 2,000. When the molecular weight is smaller than 2,000, the dispersion-stabilizing effect is reduced.

The vinyl alcohol polymers are those which have vinyl alcohol units, are substantially soluble in water and, when they are used in polymerization, are capable of forming a stable polymer latex. Such vinyl alcohol polymers can easily be made by, for example, a process wherein a vinyl ester polymer is prepared by polymerizing a vinyl monomer composition comprising a vinyl ester monomer or monomers as principal ingredient by a publicly known procedure (namely, a homopolymer of a vinyl ester monomer, a copolymer of at least two kinds of vinyl ester monomers or a copolymer of a vinyl ester monomer with other ethylenically unsaturated monomer is prepared), and then, the vinyl ester polymer is saponified by an ordinary procedure. Vinyl alcohol polymers having a modifying group such as a mercapto group having introduced to their side chains or at terminals can also be used.

The vinyl ester monomers can be used provided that they are capable of being radically polymerized, and, as specific examples thereof, there can be mentioned vinyl formate, vinyl acetate, vinyl propionate, isopropenyl acetate, vinyl valerate, vinyl caprate, vinyl laurate, vinyl stearate, vinyl benzoate, vinyl versatate and vinyl pivalate. Of these, vinyl acetate is preferable because it is industrially less costly produced.

As specific examples of the monomer copolymerizable with the vinyl ester monomer, there can be mentioned olefins such as ethylene, propylene, 1-butene and isobutene; unsaturated carboxylic acids such as acrylic acid, methacrylic acid, fumaric acid, maleic acid, itaconic acid, maleic anhydride, phthalic anhydride, trimellitic anhydride and itaconic anhydride; acrylic acid esters such as methyl acrylate, ethyl acrylate, n-propyl acrylate, isopropyl acrylate, n-butyl acrylate, t-butyl acrylate, 2-ethylhexyl acrylate, dodecyl acrylate and octadecyl acrylate; methacrylic acid esters such as methyl methacrylate, ethyl methacrylate, n-propyl methacrylate, isopropyl methacrylate, n-butyl methacrylate, t-butyl methacrylate, 2-ethylhexyl methacrylate, dodecyl methacrylate and octadecyl methacrylate; unsaturated carboxylic acid esters such as dimethyl phthalate, diethyl maleate and diisopropyl itaconate; vinyl ethers such as methyl vinyl ether, n-propyl vinyl ether, isopropyl vinyl ether, n-butyl vinyl ether, isobutyl vinyl ether, t-butyl vinyl ether, dodecyl vinyl ether and stearyl vinyl ether; nitriles such as acrylonitrile and methacrylonitrile; vinyl halides such as vinyl chloride, vinylidene chloride, vinyl fluoride and vinylidene fluoride; allyl compounds such as allyl acetate and allyl chloride; sulfonic acid group-containing compounds such as ethylenesulfonic acid, allylsulfonic acid, methallylsulfonic acid and 2-acrylamide-2-methylpropanesulfonic acid; vinylsilane compounds such as vinyltrimethoxysilane; and monomers having a quaternary ammonium group such as 3-acrylamidepropyl-trimethylammonium chloride and 3-methacrylamidepropyl-trimethylammonium chloride.

The degree of saponification of the vinyl ester polymers varies depending upon the presence of a modifying group, and the kind and amount thereof, but, in view of solubility in water, the degree of saponification is preferably in the range of 40 to 99.99% by mole, more preferably 50 to 99.99% by mole, especially preferably 60 to 99.5% by mole and most preferably 80 to 95% by mole. If the degree of saponification is too small, the dispersion stability of polymer particles is reduced. The hydroxyl value of this vinyl alcohol polymer is in a range of about 350 to 1,270 KOHmg/g, preferably about 550 to 1,200 KOHmg/g.

The vinyl ester polymer preferably has a viscosity average degree of polymerization in the range of 50 to 8,000, more preferably 100 to 6,000 and especially preferably 500 to 3,000. When the degree of polymerization is too low, the stability of polymerization is poor. In contrast, when the degree of polymerization is too high, the polymer latex has a very high viscosity and the removal of heat upon polymerization for producing the latex becomes difficult.

The above-mentioned alkali-soluble polymer having an alcoholic hydroxyl group (hereinafter referred to as "hydroxyl group-containing alkali-soluble polymer" when appropriate) is prepared by neutralizing with a base a polymer preferably having a hydroxyl value in the range of 200 to 450 KOHmg/g, more preferably 300 to 440 KOHmg/g and especially preferably 400 to 430 KOHmg/g, and preferably having an acid value in the range of 50 to 300 KOHmg/g, more preferably 60 to 200 KOHmg/g and especially preferably 70 to 150 KOHmg/g. When the hydroxyl value and the acid value are too small, the stability of monomers at polymerization is reduced. In contrast, when the hydroxyl value and the acid value are too large, the coating layer is poor in practical characteristics such as water resistance and drying property.

The hydroxyl group-containing alkali-soluble polymer preferably has a weight average molecular weight in the range of 2,000 to 100,000, more preferably 2,000 to 50,000 and especially preferably 2,000 to 20,000. With a decrease of the weight average molecular weight, the stability of monomers at polymerization is decreased. In contrast, with an increase of the weight average molecular weight, the polymer latex becomes very viscous and the removal of heat upon polymerization for producing the latex becomes difficult.

The hydroxyl group-containing alkali-soluble polymer is prepared by, for example, copolymerizing an alcoholic hydroxyl group-containing ethylenically unsaturated monomer with an ethylenically unsaturated acid monomer and then neutralizing the obtained copolymer with a base.

The alcoholic hydroxyl group-containing ethylenically unsaturated monomer is a monomer having at least one alcoholic hydroxyl group in one molecule, and includes, for example, ethylenically unsaturated monocarboxylic acid ester monomers, ethylenically unsaturated polycarboxylic acid ester monomers, ethylenically unsaturated monocarboxylic acid amide monomers, vinyl ether monomers, vinyl ketone monomers and aromatic vinyl monomers. As specific examples of the alcoholic hydroxyl group-containing ethylenically unsaturated monomer, there can be mentioned ethylenically unsaturated monocarboxylic acid ester monomers such as hydroxymethyl acrylate, 2-hydroxyethyl acrylate, 2-hydroxypropyl acrylate, 3-hydroxypropyl acrylate, 3-chloro-2-hydroxypropyl acrylate, 3-phenoxy-2-hydroxypropyl acrylate, glycerol monoacrylate, hydroxybutyl acrylate, hydroxyhexyl acrylate, hydroxyoctyl acrylate, hydroxymethyl methacrylate, 2-hydroxyethyl methacrylate, 2-hydroxypropyl methacrylate, 3-hydroxypropyl methacrylate, 3-chloro-2-hydroxypropyl methacrylate, 3-phenoxy-2-hydroxypropyl methacrylate, glycerol monomethacrylate, hydroxybutyl methacrylate, hydroxyhexyl methacrylate and hydroxyoctyl methacrylate; ethylenically unsaturated monocarboxylic acid amide monomers such as N-methylolacrylamide, N,N'-dimethylolacryamide, N-2-hydroxyethylacrylamide, N-2-hydroxypropylacrylamide, N-3-hydroxypropylacrylamide, N-methylolmethacrylamide, N,N'-dimethylolmethacryamide, N-2-hydroxyethylmethacrylamide, N-2-hydroxypropylmethacrylamide and N-3-hydroxypropylmethacrylamide; ethylenically unsaturated polycarboxylic acid ester monomers such as di-(ethylene glycol) itaconate, di(propylene glycol) itaconate, bis(2-hydroxypropyl) itaconate, bis(2-hydroxyethyl) itaconate, bis (2-hydroxyethyl) fumarate and bis(2-hydroxyethyl) maleate; vinyl ether monomers such as 2-hydroxyethyl vinyl ether; vinyl ketone monomers such as hydroxymethyl vinyl ketone; aromatic vinyl monomers such as hydroxymethylstyrene; and allyl alcohol. Of these, ethylenically unsaturated monocarboxylic acid ester monomers and ethylenically unsaturated monocarboxylic acid amide monomers are preferable. More specifically ethylenically unsaturated monocarboxylic acid ester monomers such as 2-hydroxyethyl acrylate and 2-hydroxyethyl methacrylate are preferable.

The alcoholic hydroxyl group-containing ethylenically unsaturated monomer may be used either alone or as a combination of at least two thereof. The amount of the alcoholic hydroxyl group-containing ethylenically unsaturated monomer is such that a hydroxyl group-containing alkali-soluble polymer having a desired hydroxyl value is obtained.

The ethylenically unsaturated acid monomer is not particularly limited provided that it is an ethylenically unsaturated acid monomer having an acid group such as, for example, a carboxyl group, a sulfonic acid group or a phosphoric acid group. The ethylenically unsaturated acid monomer includes, for example, an ethylenically unsaturated carboxylic acid monomer, an ethylenically unsaturated sulfonic acid monomer and a phosphorus-containing ethylenically unsaturated acid monomer.

As specific examples of the ethylenically unsaturated carboxylic acid monomer, there can be mentioned ethylenically unsaturated monocarboxylic acids such as acrylic acid, methacrylic acid and crotonic acid; ethylenically unsaturated polycarboxylic acids such as fumaric acid, maleic acid, itaconic acid and butenetricarboxylic acid; and partially esterified products of ethylenically unsaturated polycarboxylic acids such as monoethyl maleate and monomethyl itaconate.

As specific examples of the ethylenically unsaturated sulfonic acids, there can be mentioned ethylenically unsaturated sulfonic acids such as vinylsulfonic acid, styrenesulfonic acid, allylsulfonic acid and methallylsulfonic acid; and 2-acrylamide-2-methylpropanesulfonic acid, 2-acrylamide-2-hydroxypropanesulfonic acid, 3-sulfopropyl acrylate, 3-sulfopropyl methacrylate, and bis(3-sulfopropyl) itaconate.

As specific examples of the phosphorus-containing ethylenically unsaturated acid monomer, there can be mentioned vinylphosphonic acid, vinyl phosphate, bis (methacryloyloxy-ethyl) phosphate, diphenyl-2-methacryloyloxyethyl phosphate, dibutyl-2-methacryloyloxyethyl phosphate and dioctyl-2-methacryloyloxyethyl phosphate.

These ethylenically unsaturated acid monomers may be used in the form of an alkali metal salt or an ammonium salt.

The ethylenically unsaturated acid monomer may be used either alone or as a combination of at least two thereof. Of the ethylenically unsaturated acid monomers, ethylenically unsaturated carboxylic acid monomers are preferable.

Ethylenically unsaturated monocarboxylic acids such as acrylic acid and methacrylic acid are especially preferable. Acrylic acid is most preferable. The amount of ethylenically unsaturated acid monomer may be chosen so as to obtain a hydroxyl group-containing alkali-soluble polymer having a desired acid value.

The alcoholic hydroxyl group-containing ethylenically unsaturated monomer and the ethylenically unsaturated acid monomer may be copolymerized with other monomer copolymerizable therewith, provided that the effect of the present invention is not injured. As specific examples of such copolymerizable monomers, there can be mentioned aromatic vinyl monomers such as styrene, α-methylstyrene, vinyltoluene and chlorostyrene; ethylenically unsaturated monocarboxylic acid ester monomers such as methyl acrylate, ethyl acrylate, propyl acrylate, butyl acrylate, 2-ethylhexyl acrylate, trifluoroethyl acrylate, tetrafluoropropyl acrylate, methoxymethyl acrylate, ethoxyethyl acrylate, cyanomethyl acrylate, 2-cyanoethyl acrylate, glycidyl acrylate, methyl methacrylate, ethyl methacrylate, propyl methacrylate, butyl methacrylate, 2-ethylhexyl methacrylate, trifluoroethyl methacrylate, tetrafluoropropyl methacrylate, methoxymethyl methacrylate, ethoxyethyl methacrylate, cyanomethyl methacrylate, 2-cyanoethyl methacrylate and glycidyl methacrylate; ethylenically unsaturated polycarboxylic acid ester monomers such as dibutyl maleate, dibutyl fumarate and diethyl maleate; ethylenically unsaturated carboxylic acid amide monomers such as acrylamide, N-methoxymethylacrylamide, methacrylamide and N-methoxymethylmethacrylamide; and ethylenically unsaturated nitrile monomers such as acrylonitrile, methacrylonitrile, fumaronitrile, α-chloroacrylonitrile and α-cyanoethylacrylonitrile.

The process for producing a hydroxyl group-containing alkali-soluble polymer used in the present invention is not particularly limited. For example, said polymer is obtained by a process wherein a mixture comprising an alcoholic hydroxyl group-containing ethylenically unsaturated monomer, an ethylenically unsaturated acid monomer and an optional other copolymerizable monomer is copolymerized by a conventional procedure in an aqueous medium, namely, water or a mixture comprising water and an optional water-soluble organic solvent such as an alcohol, and then the acid groups contained in the resulting copolymer are partially or completely neutralized with a base.

A polymerization initiator used for the production of the hydroxyl group-containing alkali-soluble polymer includes, for example, inorganic peroxides such as sodium persulfate, potassium persulfate, ammonium persulfate, potassium perphosphate and hydrogen peroxide; organic peroxides such as diisopropylbenzene hydroperoxide, cumene hydroperoxide, t-butyl hydroperoxide, 1,1,3,3-tetramethyl hydroperoxide, 2,5-dimethylhexane-2,5-dihydroperoxide, di-t-butyl peroxide, di- α-cumyl peroxide, acetyl peroxide, isobutyryl peroxide and benzoyl peroxide; and azo compounds such as azobisisobutyronitrile, azobis-2,4-dimethylvarelonitrile and methyl azobisisobutyrate. These polymerization initiators may be used either alone or as a combination of at least two thereof. The amount of polymerization initiator varies depending upon the kind thereof, but is usually in the range of 0.1 to 20 parts by weight, preferably 0.2 to 10 parts by weight, based on 100 parts by weight of the monomers. The polymerization initiator may be added either at once at the commencement of polymerization or in lots.

The polymerization initiator may be used as a redox catalyst, namely, a combination thereof with a reducing agent. The reducing agent used in the redox catalyst includes, for example, a compound containing a metal ton in a reduced state, such as ferrous sulfate and cuprous naphthenate; a sulfonic acid compound such as sodium methanesulfonate; and an amine compound such as dimethylaniline. These reducing agents may be used either alone or as a combination of at least two thereof. The amount of reducing agent varies depending upon the kind thereof, but is preferably in the range of 0.03 to 10 parts by weight per part by weight of the polymerization initiator.

An emulsifier may be used at polymerization for producing a hydroxyl group-containing alkali-soluble polymer, although it is not indispensable. The emulsifier used includes conventional emulsifiers such as a polymerizable emulsifier which is a surface active agent having at least one polymerizable carbon-carbon double bond in the molecule, and nonionic, anionic, cationic and amphoteric surface active agents. Of these, a polymerizable emulsifier is preferable.

As specific examples of the polymerizable emulsifier, there can be mentioned anionic polymerizable emulsifiers such as propenyl-2-ethylhexylbenzenesulfosuccinic acid ester sodium salt, acrylic acid polyoxyethylene sulfate ester, methacrylic acid polyoxyethylene sulfate ester, polyoxyethylene-alkyl-propenyl-ether ammonium sulfate ester salts, acrylic acid polyoxyethylene phosphate ester and methacrylic acid polyoxyethylene phosphate ester; and nonionic polymerizable emulsifiers such as polyoxyethylene-alkylbenzene-ether acrylate esters, polyoxyethylene-alkylbenzene-ether methacrylate esters, polyoxyethylene-alkyl-ether acrylate esters and polyoxyethylene-alkyl-ether methacrylate esters.

As specific examples of the anionic surface active agent, there can be mentioned higher alcohol sulfate esters, alkylbenzenesulfonic acid salts, aliphatic sulfonic acid salts, polyoxyethylene-alkyl-arylsulfonic acid salts and polyphosphoric acid salt. As specific examples of the nonionic surface active agent, there can be mentioned polyethylene glycol alkyl esters, polyethylene glycol alkylphenyl ethers and polyethylene glycol alkyl ethers. As specific examples of the cationic surface active agent, there can be mentioned aliphatic amine salts and their quaternary ammonium salts, aromatic quaternary ammonium salts and heterocyclic quaternary ammonium salts. As specific examples of the amphoteric surface active agent, there can be mentioned carboxybetain, sulfobetaine, amino carboxylic acid salts and imidazoline derivatives.

These emulsifiers may be used either alone or as a combination of at least two thereof. The amount of emulsifier used is usually in the range of 0.01 to 2 parts by weight based on 100 parts by weight of the monomers.

A chain transfer agent may be used at polymerization for producing a hydroxyl group-containing alkali-soluble polymer. As specific examples of the chain transfer agent, there can be mentioned mercapto group-containing compounds such as mercaptans (such as n-hexylmercaptan, n-octylmercaptan, t-octylmercaptan, n-dodecylmercaptan, t-dodecyl-mercaptan and n-stearylmercaptan), thioglycolic acid, thiomalic acid and 2-ethylhexyl thioglycolate; xanthogen compounds such as dimethylxanthogen disulfide and diisopropylxanthogen disulfide; α-methylstyrene dimer and its derivatives such as 2,4-diphenyl-4-methyl-1-pentene, 2,4-diphenyl-4-methyl-2-pentene and 1,1,3-trimethyl-3-phenylindane; terpinolene; thiuram compounds such as tetramethylthiuram disulfide, tetraethylthiuram disulfide and tetramethylthiuram monosulfide; phenolic compounds such as 2,6-di-t-butyl-4-methylphenol and styrenated phenol, allyl compounds such as allyl alcohol, acrolein and methacrolein; halogenated hydrocarbon compounds such as dichloromethane, dibromomethane, carbon tetrachloride and carbon tetrabromide; vinyl ethers such as α-benzyloxystyrene, α-benzyloxyacrylonitrile and α-benzyloxyacrylamide; and triphenylethane and pentaphenylethane.

Of these, mercapto group-containing compounds are preferable because of high efficiency for chain transfer. As the mercapto group-containing compounds, those which have not larger than 50 carbon atoms, especially not larger than 20 carbon atoms, are preferable. As specific examples of the preferable mercapto group-containing compounds, there can be mentioned alkylmercaptans such as n-octylmercapan, n-dodecylmercaptan and t-dodecylmercaptan; and 2-mercatoethanol and 3-mercaptopropionic acid.

The amount of chain transfer agent is usually in the range of 0.01 to 10 parts by weight based on 100 parts by weight of the monomers. The kind and amount of chain transfer agent may be appropriately chosen so as to obtain a hydroxyl group-containing alkali-soluble polymer having a desired molecular weight. The procedure for adding the chain transfer agent is not particularly limited, and it may be added at once, or intermittently or continuously to a polymerization system.

As for polymerization conditions, the polymerization temperature is usually in the range of 0 to 100° C., preferably 30 to 90° C., and the polymerization time is usually in the range of about 10 minutes to 5 hours.

The base used for neutralization includes alkali metal hydroxides such as sodium hydroxide and potassium hydroxide; alkaline earth metal hydroxides such as calcium hydroxide and magnesium hydroxide; ammonia; amines such as methylamine, ethylamine, isopropylamine, dimethylamine, N,N-dimethylethanolamine, diisopropylamine, trimethylamine and triethanolamine. Of these, amines and ammonia are preferable. Ammonia is especially preferable. Of these, water-soluble bases may be used as an aqueous solution. When the acid groups contained in the copolymer are partially neutralized, neutralization is carried out to an extent such that the degree of neutralization is preferably at least 70% by mole, more preferably at least 90% by mole.

The composition of a polymer constituting the polymer latex used in the present invention is not particularly limited, and the polymer includes, for example, a styrene-butadiene copolymer, an acrylonitrile-butadiene copolymer, polymers of acrylic acid derivatives and polymers of methacrylic acid derivatives. However, when a coating layer having a high light resistance is required, a polymer having no conjugated diene units is preferably used.

The monomers used for making the polymer latex include, for example, conjugated diene monomers, ethylenically unsaturated carboxylic acid monomers, aromatic vinyl monomers, ethylenically unsaturated carboxylic acid ester monomers, ethylenically unsaturated carboxylic acid amide monomers and ethylenically unsaturated nitrile monomers. Of these, ethylenically unsaturated carboxylic acid ester monomers are preferably used as a principal ingredient.

As specific examples of the conjugated diene monomer, there can be mentioned 1,3-butadiene, isoprene, 2,3-dimethyl-1,3-butadiene, 1,3-pentadiene and chloroprene. Of these, 1,3-butadiene is preferable. The conjugated diene monomer is used usually in an amount of 0 to 90% by weight, preferably 0 to 80% by weight, based on the total monomers. When the amount of conjugated diene monomers is too large, the resulting coated article cannot easily be donned and put off, and has poor anti-blocking property.

As specific examples of the ethylenically unsaturated carboxylic acid monomer, there can be mentioned ethylenically unsaturated monocarboxylic acids such as acrylic acid, methacrylic acid and crotonic acid; ethylenically unsaturated polycarboxylic acids such as fumaric acid, maleic acid, itaconic acid and butenetricarboxylic acid; and partially esterified products of ethylenically unsaturated polycarboxylic acids such as monoethyl maleate and monomethyl itaconate. The ethylenically unsaturated carboxylic acid monomer is used usually in an amount of 0 to 20% by weight, preferably 0 to 10% by weight, based on the total monomers. When the amount of ethylenically unsaturated carboxylic acid monomer is too large, fine particles contained in an inner coating layer of the resulting coated article tends to be easily released, and the coated article has poor water resistance.

As specific examples of the aromatic vinyl monomer, there can be mentioned styrene, α-methylstyrene, vinyltoluene, chlorbstyrene and hydroxymethylstyrene. The aromatic vinyl monomer is used usually in an amount of 0 to 80% by weight, preferably 0 to 75% by weight, based on the total monomers. When the amount of aromatic vinyl monomer is too large, fine particles contained in an inner coating layer of the resulting coated article tends to be easily released (which tendency is hereinafter referred to as "fine particles-releasability" when appropriate).

The ethylenically unsaturated carboxylic acid ester monomer is an ester of an ethylenically unsaturated monocarboxylic acid or an ethylenically unsaturated polycarboxylic acid with an alcohol which may have a substituent such as halogen. As specific examples of the ethylenically unsaturated monocarboxylic acid ester monomer, there can be mentioned methyl acrylate, ethyl acrylate, propyl acrylate, butyl acrylate, 2-ethylhexyl acrylate, trifluoroethyl acrylate, tetrafluoropropyl acrylate, methoxymethyl acrylate, ethoxyethyl acrylate, cyanomethyl acrylate, 2-cyanoethyl acrylate, 2-hydroxyethyl acrylate, glycidyl acrylate, methyl methacrylate, ethyl methacrylate, propyl methacrylate, butyl methacrylate, 2-ethylhexyl methacrylate, trifluoroethyl methacrylate, tetrafluoropropyl methacrylate, methoxymethyl methacrylate, ethoxyethyl methacrylate, cyanomethyl methacrylate, 2-cyanoethyl methacrylate, 2-hydroxyethyl methacrylate and glycidyl methacrylate. As specific examples of the ethylenically unsaturated polycarboxylic acid ester monomer, there can be mentioned dibutyl maleate, dibutyl fumarate and diethyl maleate. The amount of these ethylenically unsaturated carboxylic acid ester monomers is not particularly limited. A preferable copolymer can be made only from a combination of these ethylenically unsaturated carboxylic acid ester monomers.

As specific examples of the ethylenically unsaturated carboxylic acid amide monomer, there can be mentioned acrylamide, N-methylolacrylamide, N,N-dimethylolacryamide, N-methoxynfethylacrylamide, methacrylamide, N-methylolmethacrylamide, N,N-dimethylolmethacryamide and N-methoxymethylmethacrylamide. The ethylenically unsaturated carboxylic acid amide monomer is used usually in an amount of 0 to 10% by weight, preferably 0 to 5% by weight, based on the total monomers. When the amount of ethylenically unsaturated carboxylic acid amide monomer is too large, fine particles-releasability becomes large.

As specific examples of the ethylenically unsaturated nitrile monomer, there can be mentioned acrylonitrile, methacrylonitrile, fumaronitrile, α-chloroacrylonitrile and α-cyanoethylacrylonitrile. The ethylenically unsaturated nitrile monomer is used usually in an amount of 0 to 50% by weight, preferably 0 to 40% by weight, based on the total monomers. When the amount of ethylenically unsaturated nitrile monomer is too large, the resulting coated article is undesirably colored, and fine particles-releasability becomes large.

The polymer latex used in the present invention preferably has an average particle diameter in the range of 10 to 5,000 nm, more preferably 30 to 2,000 nm and especially preferably 50 to 1,000 nm. With a decrease of the average particle diameter, the polymerization liquid is liable to become viscous and the handling thereof tends to become difficult. In contrast, with an increase of the average particle diameter, a uniform coating layer becomes difficult to form.

The polymer constituting the polymer latex usually has a glass transition temperature of −50 to 100° C. If the glass transition temperature is too low, an inner coating layer of the coated article becomes sticky, and the coated article cannot easily be donned and put off, and has poor anti-blocking property. In contrast, if the glass transition temperature is too high, when a coated article is drawn, fine cracks are liable to occur in an inner coating layer and the inner coating layer tends to be separated from a dip-formed article.

In a process for producing the polymer latex, a polymerization initiator can be used, which includes those recited above as examples of the polymerization initiator used for the production of a hydroxyl group-containing alkali-soluble polymer. Among the above-recited polymerization initiators, water-soluble peroxides are preferable. A persulfuric acid salt is especially preferable. The amount of polymerization initiator is usually in the range of 0.05 to 3 parts by weight, preferably 0.1 to 2 parts by weight, based on 100 parts by weight of the monomers.

The procedure of adding the polymerization initiator is not particularly limited. For example, there can be employed a procedure wherein the total amount of polymerization initiator is put at once in a polymerization vessel before commencement of polymerization; a procedure wherein a part of the polymerization initiator is put in a polymerization vessel before commencement of polymerization, and, when a predetermined time elapses from the commencement of polymerization, the residual part of polymerization initiator is added; and a procedure wherein a part of the polymerization initiator is put in a polymerization vessel before commencement of polymerization, and, the residual part of polymerization initiator is intermittently or continuously added during polymerization.

If desired, a chain transfer agent can be used. As the chain transfer agent, those which are recited above as examples of the chain transfer agent used for the production of a hydroxyl group-containing alkali-soluble polymer can be used in a desired amount.

An emulsifier may be used provided that the effect of the present invention is substantially obtained, although the emulsifier is not indispensable especially when a hydroxyl group-containing alkali-soluble polymer is used as a dispersion stabilizer. As the emulsifier, those which are recited above as examples used for the production of a hydroxyl group-containing alkali-soluble polymer can be used in a desired amount.

The amount of monomers used in polymerization for the polymer latex is preferably in the range of 10 to 80 parts by weight, more preferably 20 to 70 parts by weight, based on 100 parts by weight of the aqueous medium used for polymerization. The polymerization temperature is usually in the range of 0 to 100° C., preferably 30 to 90° C. The polymerization time is usually in the range of 1 to 20 hours.

After commencement of polymerization, when it reaches a desired polymerization conversion, polymerization is stopped. The stopping of polymerization is conducted by adding a polymerization stopper or merely cooling the polymerization system. After termination of polymerization, unreacted monomers can be removed, if desired.

The polymerization conditions and procedures, other than those mentioned above, are not particularly limited, and can be the same as those which are employed in conventional emulsion polymerization procedures.

To the polymer latex used in the present invention, if desired, auxiliaries such as a chelating agent, a dispersant, a pH adjuster, an antiseptic agent, a plasticizer and an antifoaming agent can be added during polymerization or after polymerization.

The procedure by which the polymer latex is dispersion-stabilized with a hydroxyl group-containing water-soluble polymer includes, for example, a procedure wherein the polymerization for producing the polymer latex is carried out in the presence of a hydroxyl group-containing water-soluble polymer; a procedure wherein a polymer latex is prepared by an emulsion polymerization process using a surface active agent or by emulsifying, after polymerization, a polymer made by a polymerization process other than an emulsion polymerization process, and then, a hydroxyl group-containing water-soluble polymer is added to the resulting polymer latex; and a procedure wherein a polymer, made by a polymerization process other than an emulsion polymerization process, is emulsified in an aqueous medium by using a hydroxyl group-containing water-soluble polymer as an emulsifier. Of these, the procedure wherein the polymerization for producing the polymer latex is carried out in the presence of a hydroxyl group-containing water-soluble polymer is preferable. Especially preferably, the polymerization in this procedure is carried out in an aqueous medium.

The amount of the hydroxyl group-containing water-soluble polymer contained in the polymer latex is preferably in the range of 0.5 to 100 parts by weight, more preferably 1 to 60 parts by weight and especially preferably 2 to 20 parts by weight, based on 100 parts by weight of polymer.

In the case when a monomer or monomers for the polymer latex are polymerized in the presence of a hydroxyl group-containing water-soluble polymer, the amount of the hydroxyl group-containing water-soluble polymer used is preferably in the range of 0.5 to 100 parts by weight, more preferably 1 to 60 parts by weight, especially preferably 2 to 20 parts by weight, and most preferably 3 to 10 parts by weight, based on 100 parts by weight of the monomers. When the amount of a hydroxyl group-containing water-soluble polymer is too small, the stability of polymerization system becomes poor, and aggromerates are produced in a large amount, and the mechanical and chemical stabilities of polymer latex are reduced. In contrast, when the amount of a hydroxyl group-containing water-soluble polymer is too large, the removal of polymerization heat becomes difficult due to undesirable increase of the viscosity of polymerization system, the resulting polymer latex has too high viscosity and is difficult to handle, and an inner coating layer has poor water resistance.

As for the procedure of adding an hydroxyl group-containing water-soluble polymer, there can be employed a procedure wherein the whole amount thereof is added at once at polymerization, and a procedure wherein a part thereof is added at polymerization and the residual part is added after completion of polymerization. As examples of the procedure of adding monomers, there can be mentioned (i) a procedure wherein the entire amount of monomers are added in a lot into a polymerization vessel and then a hydroxyl group-containing water-soluble polymer is added to initiate polymerization, (ii) a procedure wherein monomers and a hydroxyl group-containing water-soluble polymer are previously mixed together in an aqueous medium to prepare an emulsion, and then, the emulsion is added in lots or continuously into a polymerization vessel to conduct polymerization, and (iii) a procedure wherein a hydroxyl group-containing water-soluble polymer is added into a polymerization vessel, and then, monomers are added in lots or continuously into the polymerization vessel to conduct polymerization.

In the case when a vinyl alcohol polymer is used as the hydroxyl group-containing water-soluble polymer, a procedure is preferably employed wherein monomers and the hydroxyl group-containing water-soluble polymer are previously mixed together in an aqueous medium to prepare an emulsion, and then, the emulsion is continuously added into a polymerization vessel to conduct polymerization. In the case when a hydroxyl group-containing alkali-soluble polymer is used, a procedure is preferably employed wherein the hydroxyl group-containing alkali-soluble polymer is added into a polymerization vessel, and then, polymerization is conducted while a monomer or monomers are continuously added into the polymerization vessel. It is especially preferable in view of enhanced productivity that the hydroxyl group-containing alkali-soluble polymer is produced and then successively this polymerization procedure is carried out.

When the polymerization is conducted while a monomer or monomers are continuously added, the rate of addition of a monomer or monomers is preferably controlled so that the polymerization conversion is kept at a value in the range of 10 to 95% by weight, preferably 20 to 93% by weight and more preferably 30 to 90% by weight, based on the weight of the monomers which have been added into a polymerization vessel. If the polymerization conversion is too small, coarse polymer particles are liable to be produced. In contrast, if the polymerization conversion is too large, the viscosity of polymerization system tends to be undesirably increased.

When a monomer or monomers are polymerized in the presence of a hydroxyl group-containing water-soluble polymer, a part of the hydroxyl group-containing water-soluble polymer is grafted with a polymer produced. In the polymer latex of the present invention, the graft ratio is preferably in the range of 0.5 to 80% by weight, more preferably 1 to 70% by weight, and especially preferably 2 to 60% by weight. The graft ratio as used herein means a ratio in % of the amount of a hydroxyl group-containing water-soluble polymer having been grafted with a polymer produced, to the amount of the monomers consumed for polymerization, namely, the amount of the polymer produced. When the graft ratio is too small, it is possible that the resulting coated article cannot easily be donned and put off, and has poor anti-blocking property. In contrast, the graft ratio is too large, the concentration of polymerization mixture must be reduced to avoid an undesirable increase of the viscosity of polymer latex.

A hydroxyl group-containing water-soluble polymer which is free, i.e., have not been grafted with a polymer produced, can be separated, for example, by centrifugal separation. That is, when a polymerization mixture is subjected to centrifugal separation, a free hydroxyl group-containing water-soluble polymer remains in the state of being dispersed in an aqueous layer and the other polymeric ingredients precipitate. By measuring the amount of the free hydroxyl group-containing water-soluble polymer, the above-mentioned graft ratio can be calculated from the measured amount of free hydroxyl group-containing water-soluble polymer, the amount of the hydroxyl group-containing water-soluble polymer charged, the amount of the monomers charged, and the polymerization conversion.

When a vinyl alcohol polymer is used as a hydroxyl group-containing water-soluble polymer, the polymerization reaction is carried out preferably in the presence of an alcohol to avoid agglomeration of polymer particles. An alcohol can be made present in a polymerization system before or at the commencement of polymerization, for example, by incorporating an alcohol before addition of a polymerization initiator in a polymerization vessel, or adding an alcohol to the polymerization system as a liquid medium or a part thereof, in which a polymerization initiator is dissolved. The alcohol used may be either monohydric or polyhydric, and is preferably soluble in water. As specific examples of the alcohol, there can be mentioned methanol, ethanol, propanol, butanol, ethylene glycol, propylene glycol and glycerol. Of these, ethanol is preferable. The amount of alcohol is preferably in the range of 1 to 50 parts by weight, more preferably 3 to 20 parts by weight, based on 100 parts by weight of the monomers.

The coating agent of the present invention preferably comprises fine inorganic or organic particles in addition to the polymer latex dispersion-stabilized with the hydroxyl group-containing water-soluble polymer.

In the case a coating agent contains no fine inorganic or organic particles, it is preferable to use a polymer having a glass transition temperature in the range of 50 to 90° C., more preferably 60 to 80° C. as the polymer constituting the polymer latex to give a coated article having good donning and putting-off properties and good anti-blocking property and exhibiting reduced fine particles-releasability.

As specific examples of the fine inorganic particles, there can be mentioned fine particles of silica, magnesium oxide and titanium dioxide. As specific examples of the fine organic particles, there can be mentioned fine particles of acrylic resins, urethane resins, polyamide resins, olefin resins, formaldehyde resins, vinyl chloride resins, vinylidene chloride resins, nylon resins, cellulosic resins, starch, and crosslinked products thereof. These fine particles may be used either alone or as a combination of at least two kinds thereof. Of these, fine organic particles are preferable in view of enhanced adhesion to the polymer latex. Acrylic resins and acryl-styrene resins are especially preferable. Preferable fine organic particles have a glass transition temperature such that the particles are capable of being semi-molten by heat generated at a step of producing a dip-formed article. Such glass transition temperature is preferably in the range of 40 to 110° C., more preferably 50 to 90° C.

The fine particles preferably have a volume average particle diameter in the range of 1 to 50 μm, more preferably 3 to 30 μm so as to give a coated article having good donning and putting-off properties. When the volume average particle diameter is smaller than 1 μm, the surface roughness of coating layer becomes undesirably small, and the coated article is liable to have poor donning and putting-off properties. In contrast, when the volume average particle diameter is larger than 50 μm, the surface roughness of an inner coating layer becomes too large and the touch of a coated article during wearing is injured. The shape of fine particles is not particularly limited, but, true sphere is preferable because of good donning and putting-off properties.

The amount of fine particles is preferably in the range of 10 to 250 parts by weight, more preferably 30 to 200 parts by weight, based on 100 parts by weight of the solid content of polymer latex. When the amount of fine particles is smaller than 10 parts by weight, a coated article with good donning and putting-off properties cannot be obtained. In contrast, when the amount of fine particles is larger than 250 parts, the anti-blocking property is enhanced, but, the inner coating layer tends to have a too low elongation to follow the elongation of coated article and the fine particles-releasability becomes large. In the case the amount of fine particles exceeds 70 parts by weight, based on 100 parts by weight of the solid content of polymer latex, if the glass transition temperature of polymer latex is controlled to a value preferably in the range of −40 to 20° C., more preferably −30 to 10° C., and especially preferably −20 to 0° C., a resulting coated article has excellent donning and putting-off properties and anti-blocking property, and the fine particles-releasability is reduced to a great extent. In this case, the amount of fine particles is preferably in the range of 80 to 200 parts by weight and more preferably 80 to 180 parts by weight, based on 100 parts by weight of the solid content of polymer latex.

The coating agent of the present invention is obtained by mixing together the above-mentioned polymer latex and, if desired, optional fine powdery particles or an aqueous dispersion thereof. The solid content of the coating agent is not particularly limited, but, is preferably in the range of 1 to 15% by weight, more preferably 5 to 10% by weight. The coating agent may further comprise additives such as a thickener, a wetting agent, an anti-foaming agent, a pH adjuster and an antioxidant, according to the need. Further, in order to improve drying property, film-forming property or other properties, hydrophilic solvents such as alcohols, Cellosolves, glycols and glycerin may be added.

The coated article of the present invention is made by coating a dip-formed article with the above-mentioned coating agent. The amount of coating agent is not particularly limited, but is preferably in the range of 0.1 to 2 g/m², more preferably 0.15 to 1.5 g/m².

As specific examples of the dip-formed article, there can be mentioned gloves, finger cots and observation balloons. These dip-formed articles are made usually by conventional direct dip-forming, cohesion dip-forming and heat-sensitive dip-forming methods. The material of dip-formed article is not particularly limited, and the dip-formed article can be made from natural rubber latex or synthetic rubber latex. As specific examples of the synthetic rubber latex, there can be mentioned styrene-butadiene copolymer latex, acrylonitrile-butadiene copolymer latex and carboxyl-modified acrylonitrile-butadiene copolymer latex.

The method of coating a dip-formed article with the coating agent usually includes, for example, a method of dipping a dip-formed article in a bath of the coating agent, and a method of applying the coating agent to a dip-formed article.

The coating of dip-formed article can be conducted at a step following a dip-forming in the course of making a coated article from raw material, or conducted on a finished and stored dip-formed article. In either case, an as-coated dip-formed article is dried to give a coated article. The coating of dip-formed article may be conducted either on one surface or both surfaces thereof, and either on the whole surface or a part of the surface thereof.

The thus-made coated article of the present invention has excellent donning and putting-off properties and anti-blocking property, and greatly reduced fine particles-releasability. Therefore, the coated article is useful as a nipple of nursing bottle, medical articles such as a dropper, a duct and a water-pillow; toys such as a balloon, dolls, and a ball, and sporting goods; industrial articles such as a pressure bag and a gas storage bag; surgical gloves, household gloves, agricultural gloves and industrial gloves; and a finger cot. Especially preferably the coated article is used as a thin glove, especially a medical glove, having a thickness of 0.1 to 0.3 mm.

The invention will now be described specifically by the following working examples that by no means limit the scope of the invention. In the working examples, % and parts are % by weight and parts by weight, respectively, unless otherwise specified.

The physical properties evaluated in examples and comparative examples are determined by the following methods.

Physical Properties of Hydroxyl Group-Containing Alkali-Soluble Polymer (1) Acid Value (KOHmg/g) and Hydroxyl Value (KOHmg/g)

Before neutralization of a hydroxyl group-containing alkali-soluble polymer with a base, the polymer is taken, and then dried under vacuum at a temperature of 60° C. for 12 hours to prepare a specimen. The acid value and hydroxyl value are measured on the specimen according to JIS K 0070.

(2) Weight Average Molecular Weight

Before neutralization of a hydroxyl group-containing alkali-soluble polymer with a base, the polymer is taken, and then dried under vacuum at a temperature of 60° C. for 12 hours to prepare a specimen. The weight average molecular weight is measured on the specimen by GPC using tetrahydrofuran as elute and from a calibration curve employing standard polystyrene.

Physical Properties of Polymer Latex (3) Volume Average Particle Diameter ($\mu$m)

The volume average particle diameter is measured by Coulter LS230 (particle size analizer available from Coulter Co.)

(4) Glass Transition Temperature (° C.)

A polymer latex is cast on a glass plate having frames at the peripheral edges. The as-cast polymer latex is left to stand in a thermo-hygrostat maintained at a temperature of 20° C. and a relative humidity of 65% for 48 hours to give a filmy specimen. The glass transition temperature is measured on the filmy specimen by using a differential scanning calorimeter ("SSC 5200" available from Seiko Instruments Inc.) at an initiation temperature of −100° C. and a temperature elevation rate of 5° C./min.

(5) Graft Ratio (%)

The solid content of polymer latex is adjusted to 10%. 60 g of the polymer latex is taken as a specimen, and subjected to centrifugal separation at a temperature of 5° C. and a revolution rate of 13,000 rpm for 60 minutes by using a centrifugal separator "H-2000" available from Kokusan Centrifugal Separator K.K. 40 g of a supernatant liquid is recovered. 40 g of distilled water is added to a sediment (20 g) and uniformly mixed together. Again, the mixture is subjected to centrifugal separation, 40 g of a supernatant is recovered, and then, 40 g of distilled water is added to a sediment. This procedure of centrifugal separation, recovery of supernatant, and addition of distilled water to sediment is repeated three times in total. The solid content of the recovered three supernatants (120 g) is measured. The measured solid content is the amount (A) of free hydroxyl group-containing water-soluble polymer. The total amount (B) of hydroxyl group-containing water-soluble polymer contained in the specimen, and the amount (C) of polymer produced are calculated from the amount of hydroxyl group-containing water-soluble polymer charged at polymerization, the amount of monomers charged and the polymerization conversion. The graft ratio (%) is calculated according to the following equation.

Graft ratio (%)=[(B−A)/C]×100

Physical Properties of Glove (6) Donning and Putting Off Properties

A glove is put on and then put off in a state such that the inner, skin-contacting surface is dry. Ease of donning and putting off the dry glove (donning and putting-off property I) is evaluated according to the following criteria. Further, a glove is filled with water and then the water is removed, and the thus-wetted glove is put on and then put off in a wet state. Ease of donning and putting off the wet glove (donning and putting-off property II) is evaluated according to the following criteria. The evaluation results are expressed by the following three ratings.

A: Donning and putting-off can be conducted easily and smoothly.

B: Donning and putting-off can be conducted with some difficulty.

C: Donning and putting-off are accompanied by difficulty.

(7) Fine Particles-Releasability

Only uncoated outer face of a glove having an inner coating layer having incorporated therein fine particles is washed with water in a clean room, and then dried in an oven maintained at 40° C. Thereafter the glove is turned over to prepare a glove specimen having the outwardly exposed inner coating layer having fine particles. The glove is placed within a clean polyethylene bag, and then the bag is crumpled twenty times. Then air within the clean room is introduced into the bag and the bag is closed. The bag is shaken ten times, and the number of fine particles released from the glove is counted by a particle number measuring device"KM-08" available from Rion Co. Ltd.

(8) Anti-block Properties

A load of 9.8 KPa is imposed from outside onto a glove having an inner coating layer whereby the inner coating layer is pressed against upon another. The pressed glove is allowed to stand for 24 hours in a thermo-hygrostat maintained at a temperature of 40° C. and a relative humidity of 95%. Thereafter the glove is taken out and the stuck portions of coating layers are peeled from each other, and the peelability is evaluated according to the following criteria. The anti-block properties are expressed by the following three ratings.

A: Peeling is easily performed

B: Large peel-strength is required

C: Peeling cannot be attained

EXAMPLE 1

A pressure-resistant reaction vessel equipped with a stirrer was charged with 90 parts of deionized water, 55 parts of butyl acrylate, 44 parts of methyl methacrylate, 1 part of methacrylic acid and 5 parts of polyvinyl alcohol ("PVA-224E" available from Kuraray Co. Ltd.; degree of polymerization: 2,400, degree of saponification: 88% by mole). The content was stirred to prepare a monomer emulsion.

Another pressure-resistant reaction vessel equipped with a stirrer was charged with 57 parts of deionized water and 8 parts of ethanol, and the temperature of the content was elevated to 80° C. While the temperature was maintained at 80° C., a polymerization initiator solution comprising 0.5 part of ammonium persulfate in 10 parts of deionized water was added. When 2 minutes elapsed from the addition of initiator, the addition of the above-mentioned monomer emulsion was commenced. The addition of monomer emulsion was continued over a period of 4 hours. After the addition of monomer emulsion, the reaction mixture was stirred further for 2 hours and then cooled to terminate polymerization. At the termination of polymerization, the polymerization conversion was 97%. Thereafter unreacted monomers were removed, and a polymer latex having a solid content of 40% and a Brookfield viscosity of 80 mPa·s was obtained. Volume average particle diameter, glass transition temperature and graft ratio of the polymer latex were determined. The results are shown in Table 1.

To the polymer latex, styrene/acrylic copolymer resin particles having a volume average particle diameter of 7 μm and a glass transition temperature of 85° C. (styrene/butyl acrylate=95%/5%; hereinafter referred to as "fine organic particles (A)") were added in an amount shown in Table 1. The amount of fine organic particles (A), shown in Table 1, was in parts by weight based on 100 parts by weight of the solid content of polymer latex. To the polymer latex having fine organic particles (A) incorporated therein, deionized water was added to obtain a coating agent (a) having a total solid content of 5%.

10 parts of sulfur, 15 parts of zinc oxide, 7 parts of titanium oxide, 0.3 part of potassium hydroxide, and 32 parts of water were mixed together to prepare a vulcanizer solution having a solid content of 50%. 7 parts by weight of the vulcanizer solution was mixed with 220 parts of dip-forming latex having a solid content of 45% to prepare a dip forming-formulation. The dip-forming latex was a carboxyl-modified acrylonitrile-butadiene copolymer latex prepared by emulsion-copolymerization of 5 parts of methacrylic acid, 28 parts of acrylonitrile and 67 parts of 1,3-butadiene.

20 parts of calcium nitrate, 0.05 part of polyoxyethylene octyl-phenyl-ether (nonionic surface active agent) and 80 parts of deionized water were mixed together to prepare a coagulant solution having a solid content of 20%. A glove form was dipped in the coagulant solution for 1 minute, and then taken out therefrom. The coagulant-applied glove form was dried at 50° C. for 3 minutes thereby to deposit the coagulant on the glove form.

The coagulant-deposited glove form was dipped in the above-mentioned dip-forming latex formulation for 10 seconds, and then taken out. The dip-forming formulation-applied glove form was then dried at 60° C. for 5 minutes.

Thereafter the glove form was dipped in the above-mentioned coating agent (a) for 10 seconds, and then taken out. The coating agent-applied glove form was dried at 70° C. for 10 minutes in a drier, and further heat-treated at 120° C. for 25 minutes to give a glove form having a solid composite rubber film on the outer periphery. The solid composite rubber film was stripped from the glove form, while the solid composite rubber film was reversed to place the first deposited rubber layer on the outer surface of the reversed composite rubber film. Thus a rubber glove having an inner coating layer was obtained. The rubber glove had a wall thickness of about 0.2 mm, and the coating layer had a weight of about 1 g/m². The thickness of glove and the weight of coating layer were the same as those in the following examples and comparative examples. The properties of the rubber glove were evaluated. The results are shown in Table 1.

EXAMPLES 2 to 8

Polymer latexes were prepared by the same procedures as described in Example 1, wherein the amount of ethanol, the composition of monomers, the amount of deionized water and the kind and amount of dispersion stabilizer were varied as shown in Table 1. "PVA-205" was polyvinyl alcohol having a polymerization degree of 550 and a saponification degree of 88% by mole, available from Kuraray Co., Ltd., and "PVA-220E" was polyvinyl alcohol having a polymerization degree of 2,000 and a saponification degree of 88% by mole, available from Kuraray Co., Ltd. The properties of these polymer latexes were evaluated. The results are shown in Table 1.

Fine organic particles (A) in an amount shown in Table 1 were incorporated in each of the polymer latexes, and deionized water was added to the polymer latex mixture to obtain coating agents (b) to (h) having a total solid content of 5%, for coating a dip-formed article therewith.

Rubber gloves were made by the same procedures as mentioned in Example 1 except that coating agents (b) to (h) were used instead of coating agent (a). The properties of the gloves were evaluated. The results are shown in Table 1.

EXAMPLE 9

A polymer latex was prepared by the same procedures as described in Example 1, wherein the amount of ethanol, the composition of monomers, the amount of deionized water and the kind and amount of dispersion stabilizer were varied as shown in Table 1.

To the polymer latex, styrene/acrylic copolymer resin particles having a volume average particle diameter of 5 μm and a glass transition temperature of 55° C. (styrene/butyl acrylate=55%/45%; hereinafter referred to as "fine organic particles (B)") were added in an amount shown in Table 1, and further deionized water was added to obtain a coating agent (1) having a total solid content of 5%, for coating a dip-formed article therewith.

A rubber glove was made by the same procedures as mentioned in Example 1 except that coating agent (i) was used instead of coating agent (a). The properties of the glove were evaluated. The results are shown in Table 1.

EXAMPLE 10

A polymer latex was prepared by the same procedures as described in Example 1, wherein the amount of ethanol, the composition of monomers, the amount of deionized water and the kind and amount of dispersion stabilizer were varied as shown in Table 1.

Deionized water was added to the polymer latex to obtain a coating agent (j) having a total solid content of 5%, for coating a dip-formed article therewith.

A rubber glove was made by the same procedures as mentioned in Example 1 except that coating agent (j) was used instead of coating agent (a). The properties of the glove were evaluated. The results are shown in Table 1.

Comparative Examples 1 and 2

Polymer latexes were prepared by the same procedures as described in Example 1, wherein ethanol was not used and monomer emulsions were prepared by using emulsifiers shown in Table 1.

To each of the polymer latexes, fine organic particles (A) in an amount shown in Table 1 were incorporated, and further deionized water was added to obtain coating agents (k) and (m) having a total solid content of 5%, for coating a dip-formed article therewith.

A rubber glove was made by the same procedures as mentioned in Example 1 except that coating agent (k) or (m) was used instead of coating agent (a). The properties of the glove were evaluated. The results are shown in Table 1.

As seen from Table 1, gloves made by using conventional low-molecular-weight emulsifiers in Comparative Examples 1 and 2 exhibit undesirably large fine particles-releasability and poor anti-blocking property.

In contrast, gloves made by using the coating agent of the present invention in Examples 1 to 10 have excellent donning and putting off properties and anti-blocking property, and exhibit greatly reduced large fine particles-releasability. Even if a coating agent having no fine organic particles incorporated therein is used, when the glass transition temperature of a polymer latex used is appropriately controlled (Example 10), the resulting glove has excellent donning and putting off properties and anti-blocking property, and exhibits greatly reduced fine particles-releasability.

TABLE 1

| | Example | | | | | | | | | | Com. Ex. | |
|---|---|---|---|---|---|---|---|---|---|---|---|---|
| | 1 | 2 | 3 | 4 | 5 | 6 | 7 | 8 | 9 | 10 | 1 | 2 |
| Ingredients added in vessel (parts) | | | | | | | | | | | | |
| D ionized water | 57 | 57 | 57 | 57 | 57 | 57 | 57 | 57 | 57 | 57 | 57 | 57 |
| Ethanol | 8 | 4 | 8 | 20 | 8 | 10 | 8 | 8 | 4 | 8 | — | — |
| Composition of monomer emulsion (parts) | | | | | | | | | | | | |
| D ionized water | 90 | 100 | 145 | 190 | 100 | 100 | 130 | 115 | 100 | 90 | 90 | 90 |
| Styrene | — | — | 30 | — | 50 | — | — | — | — | — | — | — |
| Acrylonitrile | — | — | — | — | — | 35 | 39 | — | — | — | — | — |
| Ethyl acrylate | — | — | 60 | — | — | — | — | — | — | — | — | — |
| Butyl acrylate | 55 | 65 | — | 70 | — | — | — | — | 63 | 18 | 55 | 65 |
| Methyl methacrylate | 44 | 33 | 10 | 29 | — | — | 10 | 50 | 35 | 81 | 44 | 33 |
| Methacrylic acid | 1 | 2 | — | 1 | — | — | 1 | — | 2 | 1 | 1 | 2 |
| 1,3-Butadiene | — | — | — | — | 50 | 65 | 50 | 50 | — | — | — | — |
| PVA 205 | — | — | 40 | 80 | — | — | 30 | — | — | — | — | — |
| PVA 220E | — | 10 | — | — | 10 | 10 | — | — | — | — | — | — |
| PVA 224E | 5 | — | — | — | — | — | — | 20 | 5 | 5 | — | — |
| Sodium lauryl sulfate | — | — | — | — | — | — | — | — | — | — | 5 | — |
| SPONENPS | — | — | — | — | — | — | — | — | — | — | — | 3 |
| Properties of polymer latex | | | | | | | | | | | | |
| Glass transition temperature (° C.) | 6 | −6 | 18 | −13 | −19 | −37 | −12 | −18 | −4 | 63 | 6 | −6 |
| Graft ratio (%) | 3.6 | 8.6 | 17 | 35 | 5.2 | 6.5 | 12 | 16 | 3.7 | 4.2 | — | — |
| Average particle diameter (nm) | 350 | 270 | 210 | 150 | 330 | 290 | 230 | 200 | 300 | 330 | 180 | 230 |
| Latex viscosity (mPa · s) | 80 | 250 | 1600 | 2500 | 120 | 150 | 1500 | 2200 | 110 | 90 | 10 | 25 |
| Fine particles (parts) | | | | | | | | | | | | |
| Fine organic particle (A) | 60 | 60 | 60 | 40 | 60 | 60 | 60 | 50 | — | — | 60 | 40 |
| Fine organic particle (B) | — | — | — | — | — | — | — | — | 130 | — | — | — |
| Coating agent | (a) | (b) | (c) | (d) | (e) | (f) | (g) | (h) | (i) | (j) | (k) | (m) |
| Properties of glove | | | | | | | | | | | | |
| Donning & putting off (1) | A | A | A | A | A | A | A | A | A | A | A | B |
| Donning & putting off (2) | A | A | A | B | A | A | A | A | A | A | A | A |
| Fine particles-releasability | 300 | 400 | 600 | 500 | 400 | 400 | 300 | 300 | 300 | 600 | 1500 | 1200 |
| Anti-blocking | A | A | A | A | A | A | A | A | A | A | C | C |

Note, SPONENPS: Sodium polyoxyethylene-nonyl-phenyl-ether sulfate

EXAMPLE 11

A reaction vessel equipped with a stirrer was charged with 160 parts of deionized water, 6 parts of 2-hydroxyethyl acrylate, 1 part of 2-hydroxyethylmethacrylate and 1 part of acrylic acid. The temperature of the content was elevated to 80° C., and then a solution of a polymerization initiator was added to initiate a polymerization. The polymerization initiator solution was prepared by dissolving 0.5 part of ammonium persulfate in 10 parts of deionized water. Polymerization was continued for 1 hour. When the polymerization was stopped, the polymerization conversion reached 99%. A part of the polymer produced was collected, and its properties were evaluated. The polymer had a hydroxyl value of 410 KOHmg/g, an acid value of 100 KOHmg/g and a weight average molecular weight of 2,300.

Then, to the polymer-containing reaction vessel, an aqueous 28% ammonia solution was added in an amount equivalent to acrylic acid initially charged in the reactor, whereby the polymer liquid was neutralized to obtain an aqueous solution of a hydroxyl group-containing alkali-soluble polymer.

Then, a monomer mixture comprised of 35 parts of methyl methacrylate and 65 parts of butyl acrylate was continuously added into the polymer-containing reaction vessel over a period of 4 hours while the polymerization temperature was maintained at 80° C. When the addition of monomer mixture was completed, the temperature was elevated to 85° C., and polymerization was further carried out for 2 hours. At the termination of polymerization, the polymerization conversion was 98%. Thereafter unreacted monomers were removed, and a polymer latex having a solid content of 40% and a Brookfield viscosity of 100 mPa·s was obtained. The polymer latex had a volume average particle diameter of 250 nm, a glass transition temperature of −4° C. and a graft ratio of 2.5%.

To the polymer latex, 60 parts of fine organic particles (A) was added, based on 100 parts by weight of the solid content of the polymer latex. To the polymer latex having fine organic particles (A) incorporated therein, deionized water was added to obtain a coating agent (n) having a total solid content of 5%.

A rubber glove was made by the same procedures as mentioned in Example 1 except that the above-mentioned amount of coating agent (n) was used instead of coating agent (a). The properties of the glove were evaluated. The results are shown in Table 2.

EXAMPLE 12

The procedures described in Example 1 were repeated to obtain a coating agent (p) instead of coating agent (a) wherein, instead of fine organic particles (A), fine organic particles (B) were used in an amount of 120 parts based on 100 parts of the solid content of polymer latex.

A rubber glove was made by the same procedures as mentioned in Example 1 except that the above-mentioned amount of coating agent (p) was used instead of coating agent (a). The properties of the glove were evaluated. The results are shown in Table 2.

EXAMPLE 13

The procedures described in Example 11 were repeated to obtain a polymer latex wherein a monomer mixture comprised of 82 parts of methyl methacrylate and 18 parts of butyl acrylate was used. The thus-obtained polymer latex had a solid content of 40%, a Brookfield viscosity of 120 mPa·s, a volume average particle diameter of 250 nm, a glass transition temperature of 65° C. and a graft ratio of 3.4%. Deionized water was added to the polymer latex to prepare a coating agent (q) having a solid content of 5%.

A rubber glove was made by the same procedures as mentioned in Example 1 except that the above-mentioned amount of coating agent (q) was used instead of coating agent (a). The properties of the glove were evaluated. The results are shown in Table 2.

TABLE 2

| Example No. | 11 | 12 | 13 |
|---|---|---|---|
| Properties of glove | | | |
| Donning & putting off (1) | A | A | A |
| Donning & putting off (2) | A | A | A |
| Fine particles-releasability | 400 | 300 | 600 |
| Anti-blocking | A | A | A |

As seen from Table 2, in the case where a glove is made by using a coating agent comprising a polymer latex dispersion-stabilized with an alkali-soluble polymer containing an alcoholic hydroxyl group as a water-soluble high-molecular-weight compound containing an alcoholic hydroxyl group, the resulting glove has excellent donning and putting off properties and anti-blocking property, and exhibits greatly reduced fine particles-releasability.

Industrial Applicability

According to the present invention, by coating a dip-formed article with a coating agent comprising a polymer latex dispersion-stabilized with a water-soluble high-molecular-weight compound containing an alcoholic hydroxyl group, a coated article having excellent donning and putting off properties and anti-blocking property, and exhibiting greatly reduced fine particles-releasability is obtained.

What is claimed is:

1. A coating agent comprising:
   a polymer latex and fine organic particles, said polymer latex is dispersion-stabilized with a water-soluble high-molecular weight compound having an alcoholic hydroxyl group and a weight average molecular weight of at least 2,000, and is prepared by polymerizing a monomer or monomers in the presence of said water-soluble high-molecular weight compound, and said fine organic particles have a volume average particle diameter in the range of 1 to 50 µm,
   wherein said polymer constituting the polymer latex has no conjugated diene units.

2. The coating agent according to claim 1, wherein the water-soluble high-molecular weight compound is at least one compound selected from the group consisting of vinyl alcohol polymers, alkali-soluble polymers, cellulose derivatives and starch derivatives.

3. The coating agent according to claim 1, wherein the polymer latex is dispersion-stabilized with 0.5 to 1000 parts by weight, based on 100 parts by weight of the polymer contained in the polymer latex, of the water-soluble high-molecular weight compound.

4. The coating agent according to claim 1, wherein the content of the fine particles is in the range of 10 to 250 parts by weight based on 100 parts by weight of the solid content in the polymer latex.

5. A coated article made by coating a dip-formed article with the coating agent as claimed in claim 1.

6. The coated article according to claim 5, wherein the dip-formed article is a glove.

7. The coating agent according to claim 1, wherein the polymerization of the monomer or monomers is carried out in the presence of 0.5 to 100 parts by weight, based on 100 parts by weight of the monomer of or monomers, of the water-soluble high-molecular weight compound.

8. The coating agent according to claim 1, wherein the polymer constituting the polymer latex contains ethylenically unsaturated carboxylic acid ester monomer units.

9. The coating agent according to claim 1, wherein the water-soluble high-molecular weight compound having an alcoholic hydroxyl group is a vinyl alcohol polymer or an alkali-soluble polymer having an alcoholic hydroxyl group.

10. The coating agent according to claim 1, wherein the water-soluble high-molecular weight compound having an alcoholic hydroxyl group is a vinyl alcohol polymer.

11. The coating agent according to claim 10, wherein the vinyl alcohol polymer is prepared by saponifying a vinyl ester polymer having a viscosity average degree of polymerization in the range of 50 to 8,000, and has a degree of saponification in the range of 40 to 99.99% by mole.

12. The coating agent according to claim 10, wherein the polymerization of the monomer or monomers is carried out further in the presence of an alcohol.

13. The coating agent according to claim 1, wherein the fine organic particles have a glass transition temperature in the range of 40° C. to 110° C.

14. The coating agent according to claim 1, which has a solid content in the range of 1 to 15% by weight.

15. A process for producing a coated article comprising forming a dip-formed article and coating the dip-formed article with the coating agent as claimed in claim 1.

* * * * *